(12) United States Patent
Eidinger et al.

(10) Patent No.: US 7,837,646 B2
(45) Date of Patent: Nov. 23, 2010

(54) HYDROCEPHALUS SHUNT SYSTEM QUICK CONNECTOR ASSEMBLY

(75) Inventors: Bruce Eidinger, Sutton, MA (US); Kendra McGrath, Gloucester, MA (US); Joshua Rigberg, New York, NY (US); Peter Callaway, Laguna Beach, CA (US); Mark Macomber, Norton, MA (US)

(73) Assignee: Northeastern University, Boston, MA (US)

( * ) Notice: Subject to any disclaimer, the term of this patent is extended or adjusted under 35 U.S.C. 154(b) by 104 days.

(21) Appl. No.: 11/664,434

(22) PCT Filed: Sep. 30, 2005

(86) PCT No.: PCT/US2005/035211

§ 371 (c)(1),
(2), (4) Date: Mar. 30, 2007

(87) PCT Pub. No.: WO2006/039501

PCT Pub. Date: Apr. 13, 2006

(65) Prior Publication Data

US 2008/0065000 A1   Mar. 13, 2008

Related U.S. Application Data

(60) Provisional application No. 60/614,641, filed on Sep. 30, 2004.

(51) Int. Cl.
*A61M 5/00* (2006.01)
(52) U.S. Cl. ............. 604/9; 285/319; 285/351; 285/921; 285/352
(58) Field of Classification Search ............ 604/9; 285/319, 351, 921, 352
See application file for complete search history.

(56) References Cited

U.S. PATENT DOCUMENTS

| | | | |
|---|---|---|---|
| 4,753,458 A * | 6/1988 | Case et al. | 285/93 |
| 4,846,506 A | 7/1989 | Bocson et al. | 285/4 |
| 4,867,487 A | 9/1989 | Phillis | 285/305 |
| 4,915,421 A | 4/1990 | Dennany, Jr. | 285/39 |
| 5,611,707 A | 3/1997 | Meynier | |
| 5,637,083 A | 6/1997 | Bertrand et al. | 604/9 |
| 5,947,531 A | 9/1999 | Eckard et al. | 285/319 |
| 6,012,944 A * | 1/2000 | Hatakeyama | 439/441 |
| 6,158,458 A | 12/2000 | Ryan | 137/515.5 |
| 6,234,544 B1 | 5/2001 | Bartholomew | |
| 6,250,692 B1 * | 6/2001 | Ito et al. | 285/319 |
| 6,319,231 B1 | 11/2001 | Andrulitis | |
| 6,634,679 B1 | 10/2003 | Stieler | |
| 6,733,047 B1 | 5/2004 | Stieler | |
| 6,746,056 B2 | 6/2004 | Palmer | |
| 6,780,042 B1 | 8/2004 | Badescu et al. | |

* cited by examiner

*Primary Examiner*—Tatyana Zalukaeva
*Assistant Examiner*—Ilya Y Treyger
(74) *Attorney, Agent, or Firm*—Weingarten, Schurgin, Gagnebin & Lebovici LLP

(57) ABSTRACT

A shunt system quick connector assembly to quickly connect and disconnect a catheter to a hydrocephalus shunt system comprising a valve in a valve housing. The catheter is affixed to the quick connector assembly. The quick connector assembly snaps over an external barb on the valve housing of the shunt system with an audible sound, so that the surgeon knows that connection has been made. The connector assembly can be operated quickly, minimizing the time for the surgical procedure and the opportunity for infection. The connector assembly has smooth surfaces to minimize the growing of tissue into the connection.

30 Claims, 7 Drawing Sheets

HYDROCEPHALUS SHUNT SYSTEM QUICK CONNECTOR ASSEMBLY

CROSS REFERENCE TO RELATED APPLICATIONS

Benefit is claimed under 35 U.S.C. §119(e) of U.S. Provisional Application No. 60/614,641, filed Sep. 30, 2004, the disclosure of which is incorporated by reference herein.

STATEMENT REGARDING FEDERALLY SPONSORED RESEARCH OR DEVELOPMENT

N/A

BACKGROUND OF THE INVENTION

Hydrocephalus is a disease that causes excessive cerebral spinal fluid (CSF) to build up in the ventricle of the brain. Treatment involves the surgical implantation of a shunt system into the skull to divert CSF from the ventricle to another part of the body, such as the peritoneal cavity or the right atrium of the heart. The shunt system includes a valve that regulates the flow of CSF. Two catheters are connected to the shunt: a proximal catheter inserted directly into the ventricle allows the CSF to flow into the shunt, and a distal catheter leads from the shunt under the skin to discharge the CSF to the drainage point.

The valve in the shunt system controls the direction of fluid flow and the pressure in the ventricle. A Codman Hakim programmable shunt includes a pressure differential valve the pressure of which can be adjusted non-invasively by a surgeon after implantation if necessary.

Both the proximal and distal catheters are connected to the shunt by suturing. The surgeon slips the catheter over a barb connection on the shunt and reinforces the connection with a knot above the burr.

SUMMARY OF THE INVENTION

The present invention relates to a quick connector assembly that provides a connection between a catheter and a valve housing in a hydrocephalus shunt system. In the shunt system, a barb element having a external barb protrudes from the valve housing.

The quick connector assembly includes a connector body through which a fluid passage extends. The catheter is affixed to one end of the connector body. The quick connector assembly also includes a resilient holding element comprising a radially inwardly projecting member, such as an annular snap ring, locking rib, or resilient arms. The external barb slips past the holding element with an audible sound, such as a click or snap, and is retained by the holding element with at least a portion of the barb element sealed by a sealing element within the connector body to prevent leakage of fluid. The audible sound allows the surgeon to hear when the connection has been made. The connector assembly can be disconnected by simply pulling the connector assembly away from the barb element.

The present quick connector assembly eliminates some of the time and struggle involved with suturing a catheter to the shunt. Shortening surgery time and limiting contact with the shunt system also minimizes opportunities for infection.

DESCRIPTION OF THE DRAWINGS

The invention will be more fully understood from the following detailed description taken in conjunction with the accompanying drawings in which.

DETAILED DESCRIPTION OF THE INVENTION

Figure 1:
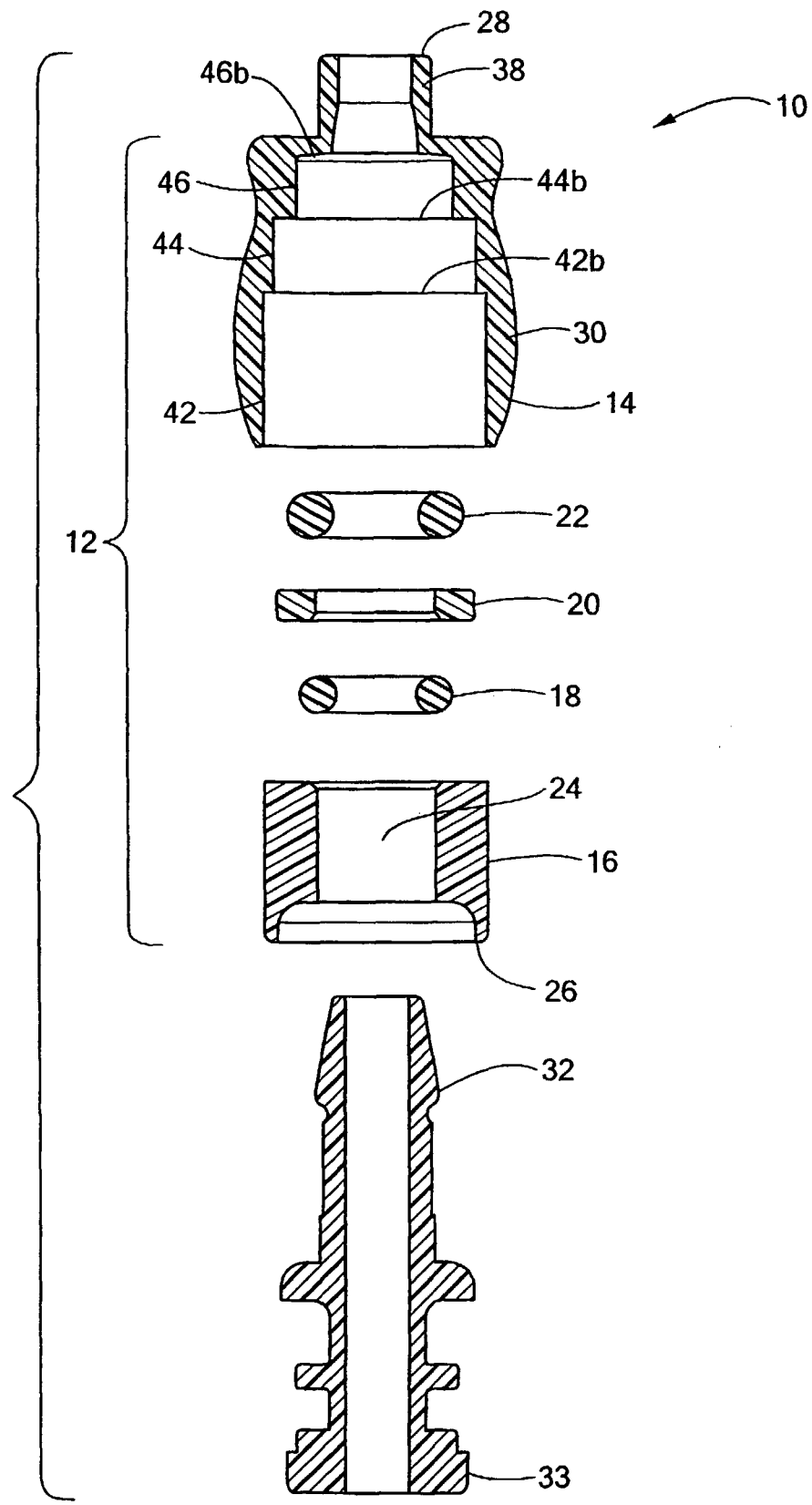
FIG. 1 is an exploded isometric view of a shunt quick connector assembly of the present invention.

The present invention relates to a quick connector assembly for use with a shunt system, such as a Codman Hakim programmable shunt or any other shunt system. Referring to the embodiment of FIGS. 1-3, a shunt system 34 includes a valve housing from which a barb element 33 protrudes. The barb element includes an external barb 32. The quick connector assembly 10 of the present invention includes a connector body 12 through which a fluid passage 24 extends. A catheter 40 is affixed to one end 38 of the connector body. At least a portion of the barb element 33 is inserted into the opposite end of the connector body and is retained therein by a resilient holding element 18. The holding element has a radially inwardly projecting member(s) (described further below) that is able to resile or spring back to its original position after passage of the external barb of the barb element. A sealing element 22 seals the barb element within the connector body to prevent leakage of fluid.

Figure 3:
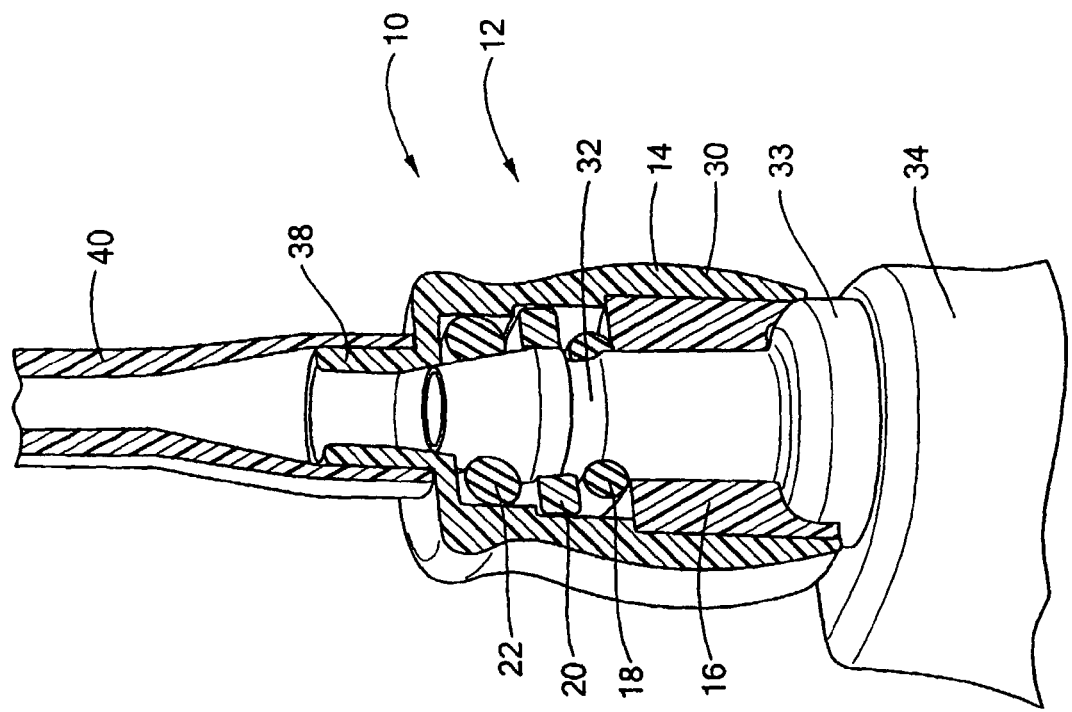
FIG. 3 is a cross sectional view of the shunt system quick connector assembly of FIG. 1 connected to a catheter and the ventricular barb element of a shunt system.
Figure 2:
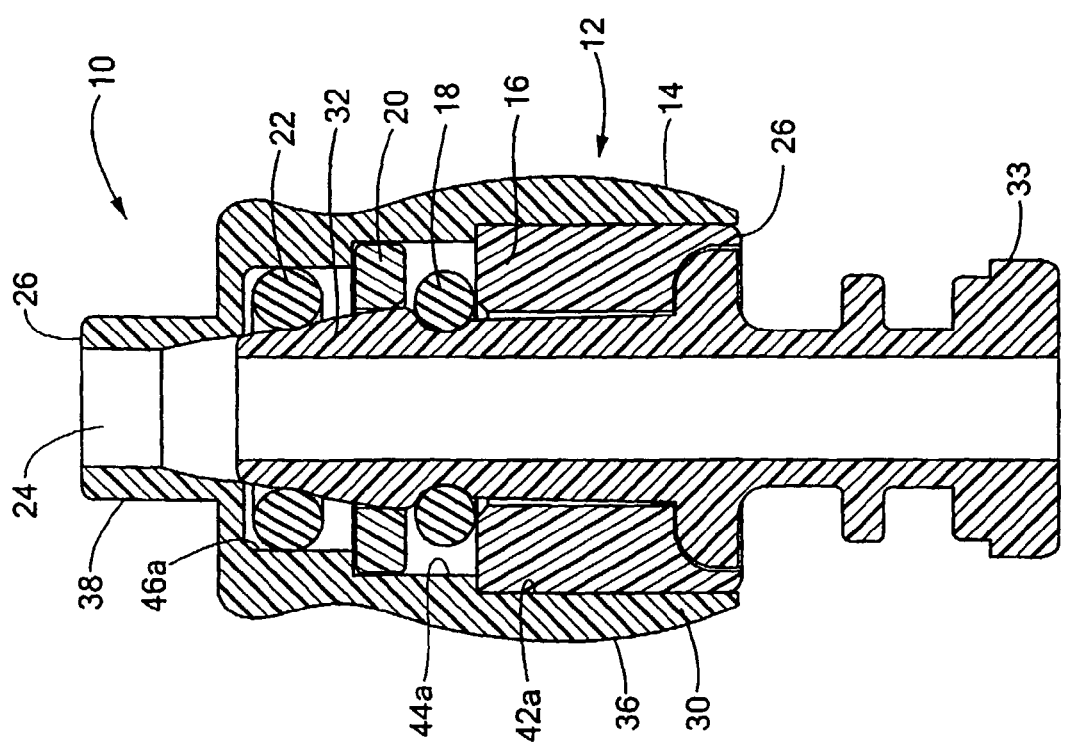
FIG. 2 is a cross sectional view of the quick connector assembly of FIG. 1 connected to a ventricular barb element of a shunt system.

More particularly, in the embodiment of FIGS. 1-3, the connector body 12 includes a main body portion 14. A retaining insert 16 for retaining the holding element, such as a snap ring 18, and a washer or retainer 20 for retaining the sealing element, such as an O-ring 22, are located within the main body portion. The fluid passageway 24 extends through the connector body from an entrance opening 26 to an exit opening 28. The main body portion includes a female portion 30 in which is inserted the barb element 33 having the external barb 32 of the shunt system 34. The female portion has a smooth outer surface 36, which keeps the connector body from being overly intrusive when implanted in a patient so that surrounding tissue is less likely to "root" in the connection. The main body portion also includes a male portion 38 that is affixed to the catheter 40, such as with a suitable adhesive. The catheter is preferably permanently affixed to the assembled connector body during manufacture.

In the embodiment illustrated, the interior of the female portion 30 of the main body portion 14 includes three sections 42, 44, 46 each defined by an interior wall 42a, 44a, 46a and separated by shoulders or steps 42b, 44b. A third shoulder or step 46b separates the third section 46 from the male portion 38. The retaining insert 16 fits snugly against the first wall 42a within the first section 42 and extends from the entrance opening 26 to the first step 42a. The retaining element is preferably affixed, such as with adhesive, to the interior of the female portion. The washer 20 fits snugly against the second wall 44a within the second section 44 and adjacent the second shoulder 44b. The O-ring 22 is located between the washer 20 and the third shoulder 46b. The O-ring prevents fluid from leaking from the barb element back through the connector assembly. The washer retains the O-ring in place within the main body portion. The retaining insert 16 is shaped to conform to the outer shape of the barb element 33, which assists in preventing bending moments from weakening the barb element 33, pulling the barb element from the quick connector assembly, or creating a gap between the barb and the sealing element.

In the embodiment illustrated, the holding element for the external barb is the snap ring 18, which is constructed of a semi-elastic, biocompatible material. The snap ring is located within the second section 44 of the female portion and is retained there by the retaining insert 16. The retaining insert keeps the snap ring from shifting axially along the main body portion. The external barb 32 of the barb element 33 is retained beneath the snap ring, thereby retaining the barb element in the connector body. The snap ring is preferably split so that it can readily expand into the annular region of the second section 44 as the barb element passes by. The holding element is resilient so that it can expand as the barb element passes by and then return to its original position to retain the barb element within the connector body.

In this manner, a shunt system with an external barb can be pushed into the connector body and can snap into place beneath the snap ring with an audible sound, assuring the surgeon that the connection has been made. To disconnect the catheter, the surgeon merely pulls on the connector assembly with a sufficient force to move the external barb past the snap ring.

Preferably, for a hydrocephalus shunt system, the quick connector assembly is able to withstand the expected pulling forces and pressures as evidenced by ISO standard 7197. This standard requires that the connector withstand a hanging 2.2 pound weight for one minute and an internal pressure of 1.75 psi for five minutes.

Figure 5:
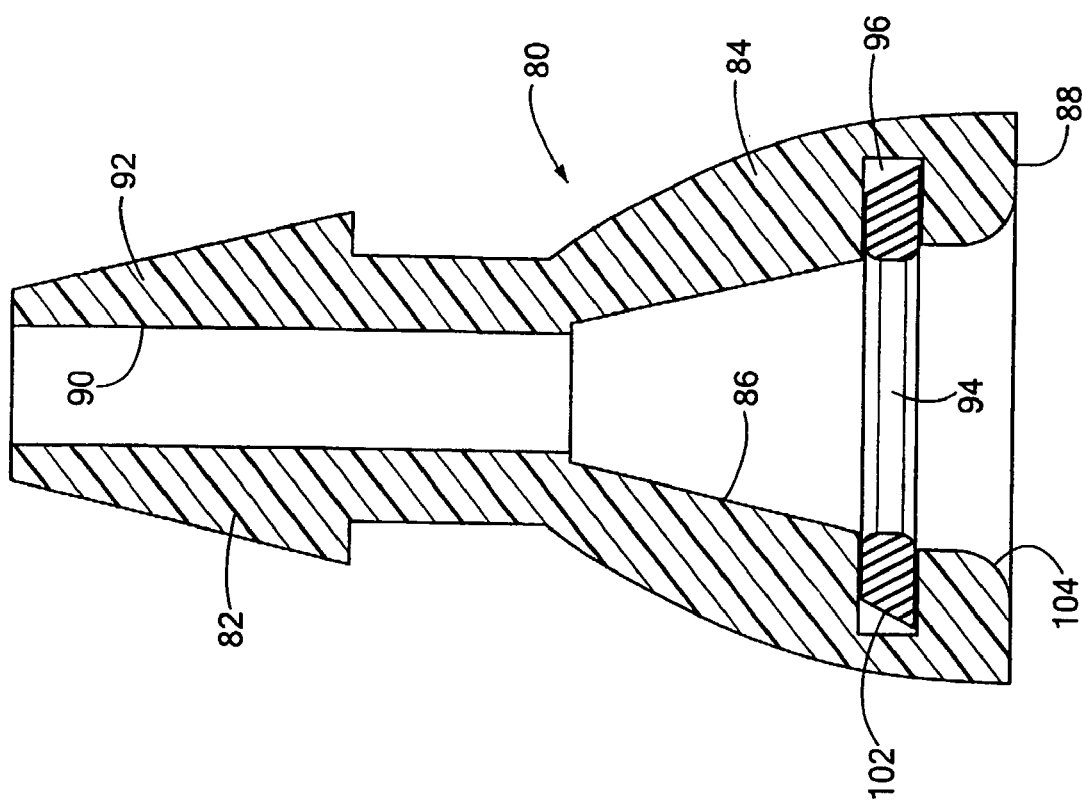
FIG. 5 is a cross sectional view of the quick connector assembly of FIG. 4.
Figure 4:
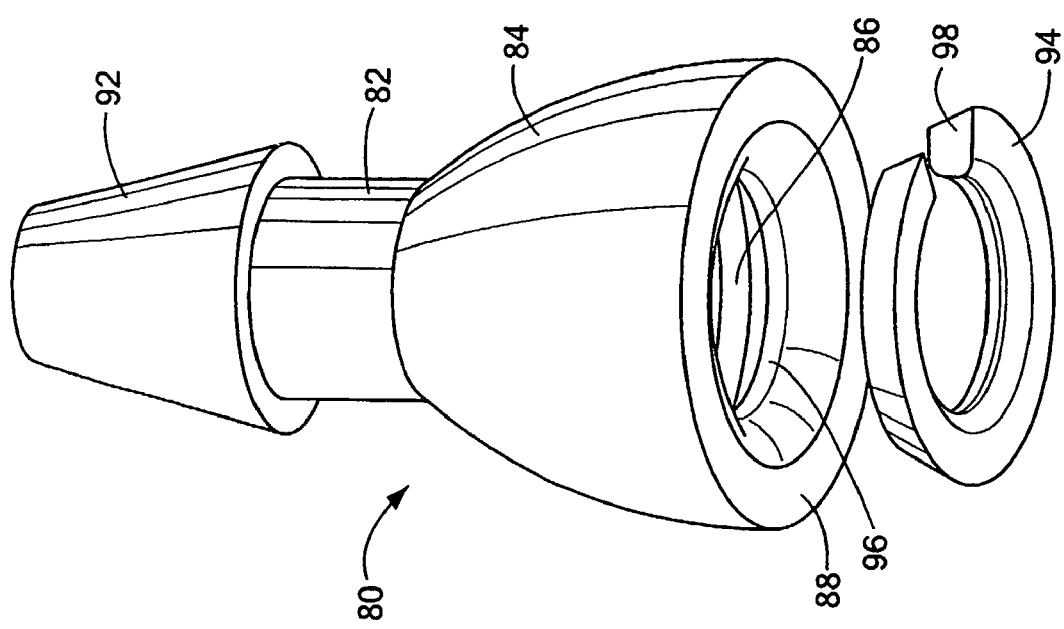
FIG. 4 is an exploded isometric view of a further embodiment of a quick connector assembly of the present invention.

In another embodiment, illustrated in FIGS. 4 and 5, a quick connector assembly 80 is formed with a single piece connector body 82. A female portion 84 includes an internal sealing surface 86 that tapers from the entrance opening 88 to a narrower portion 90 of the passage through the male portion 92. The barb element (not shown in FIGS. 4 and 5) is inserted into the female portion. The sealing surface 86 is preferably smooth to provide a fluid tight seal with the external barb. A snap ring 94 is located within an annular groove 96 formed in the internal sealing surface 86. The groove keeps the snap ring from shifting axially along the main body and also keeps tension between the barb and sealing surface to facilitate a proper seal. The external barb of the shunt is retained beneath the snap ring, thereby retaining the shunt barb in the female portion. The snap ring is preferably includes a split 98 so that it can readily expand into the annular retaining groove 96 in the connector body. The snap ring, in conjunction with the connector body, keeps the external barb of the shunt securely fixed to the smooth sealing surface within the connector body. This is accomplished because the snap ring is only able to expand and contract within the connector body when the barb is inserted into the housing. For ease of assembly, the outer edge 102 of the snap ring may be angled and the edge 104 of the entrance opening 88 of the connector body may be rounded.

Figure 6:
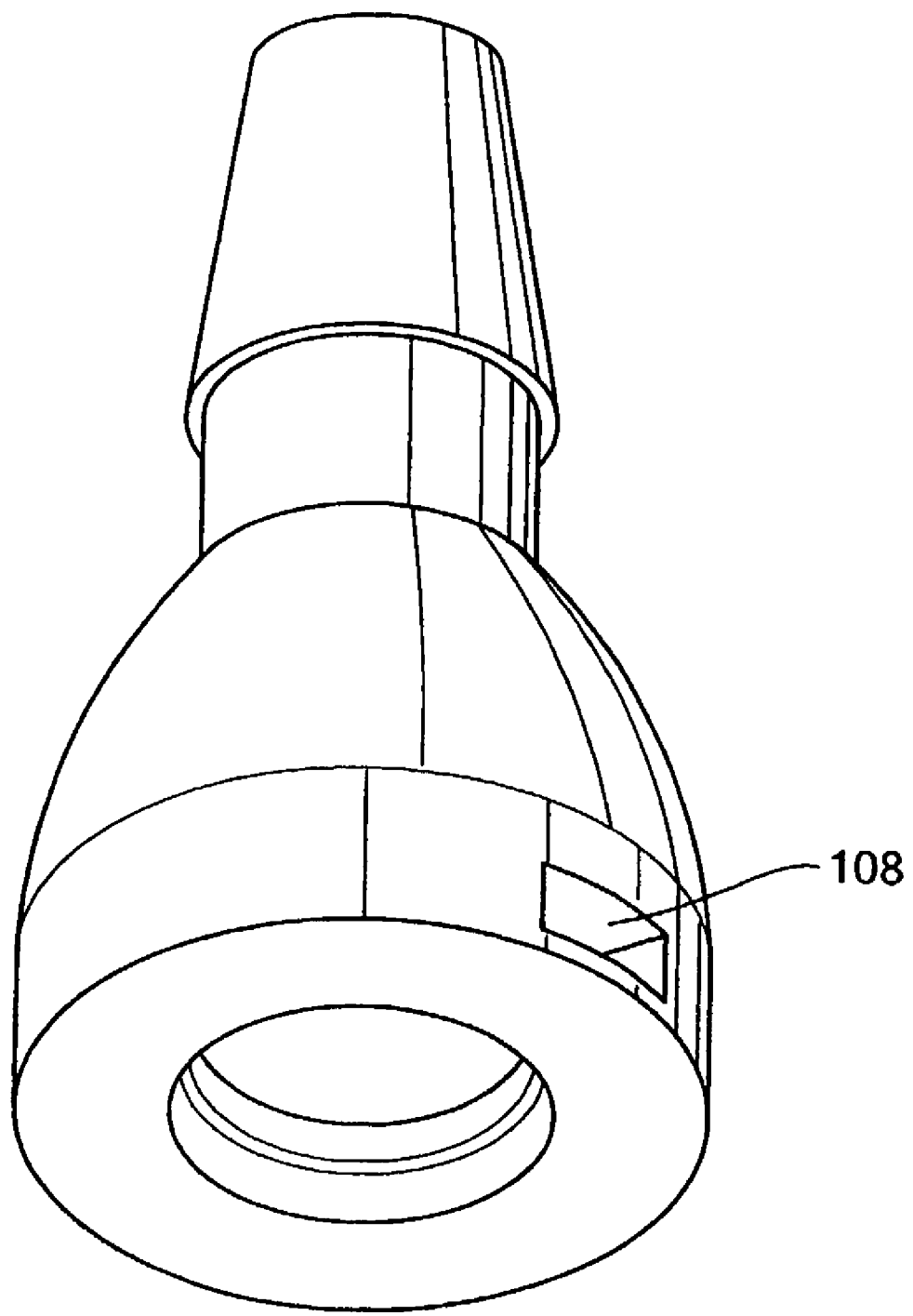
FIG. 6 is an isometric view of a yet further embodiment of a quick connector assembly of the present invention.

In another embodiment, a hole 108 may be provided through the connector body to the annular retaining groove. See FIG. 6. A tool is inserted into the hole to spread the snap ring open at the split, thereby allowing the catheter to be easily pulled out. In a further alternative, the snap ring may be formed integrally with the connector body.

Figure 7:
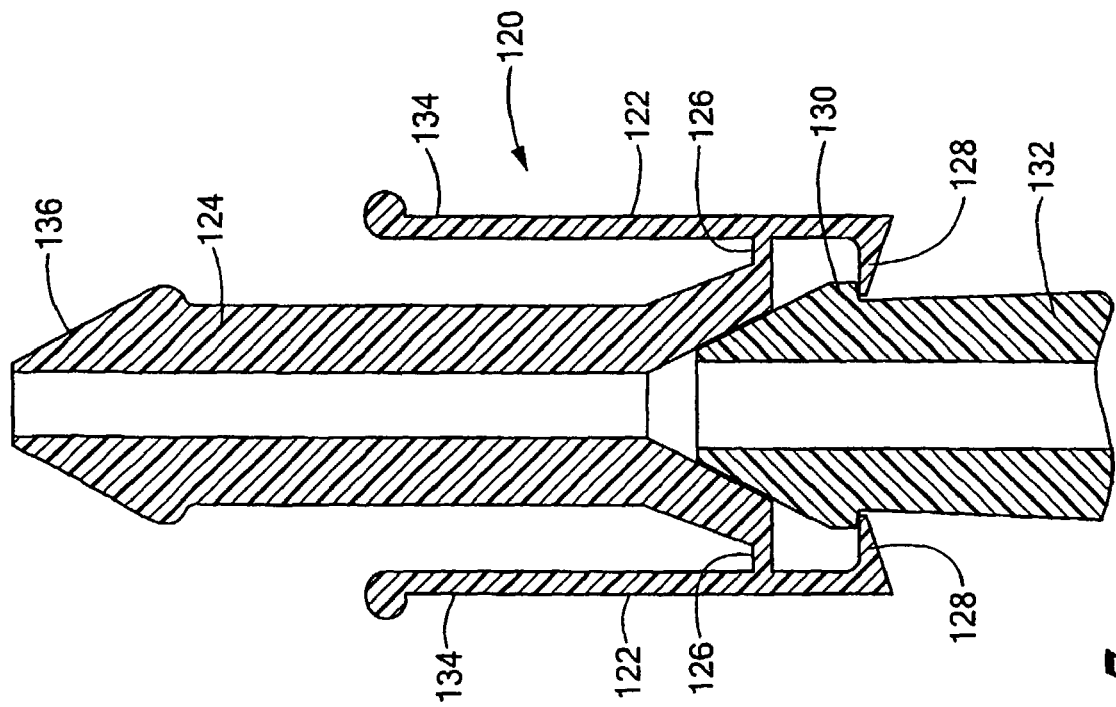
FIG. 7 is a cross sectional side view of a still further embodiment of a quick connector assembly of the present invention.

FIG. 7 illustrates a further embodiment in which a quick connector assembly 120 having a holding element in which a pair of lever arms 122 are fixed to a main body 124 of the connector assembly with resilient fulcrum extensions 126. The lower end of each lever arm includes a tooth 128 that catches under the external barb 130 of the barb element 132 of a shunt system. To disconnect the shunt system, the lever arms are squeezed inwardly about their upper ends 134. Two lever arms are shown, but any desired number could be provided, particularly if greater contact area with the barb element were desired. The interior surface is conical or tapered to sit snugly on the barb element to create a seal therewith. A catheter is affixed to the opposite end 136 of the main body 134.

Figure 8:
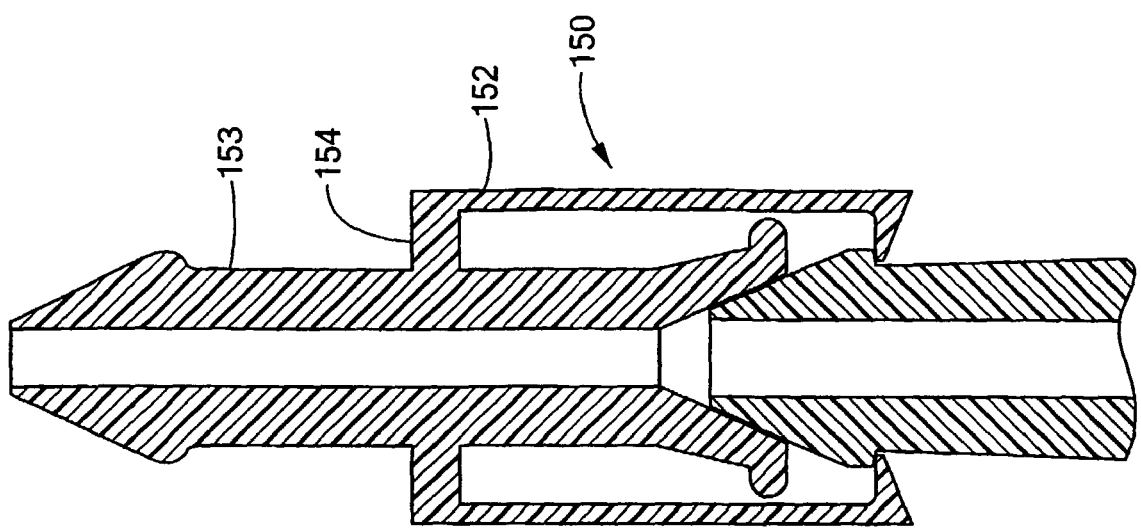
FIG. 8 is a cross sectional side view of a still further embodiment of a quick connector assembly of the present invention.

FIG. 8 illustrates a further embodiment of a quick connector assembly 150, similar to that of FIG. 7, in which locking arms 152 are connected to the connector body 153 by cross members 154. Two locking arms are shown, but any desired number could be provided, particularly if greater contact area with the barb element were desired. The cross members cover the tops of the arms to prevent or minimize the arms from snagging or catching on anything. To disconnect the connector assembly, the arms are pinched together.

Figure 10:
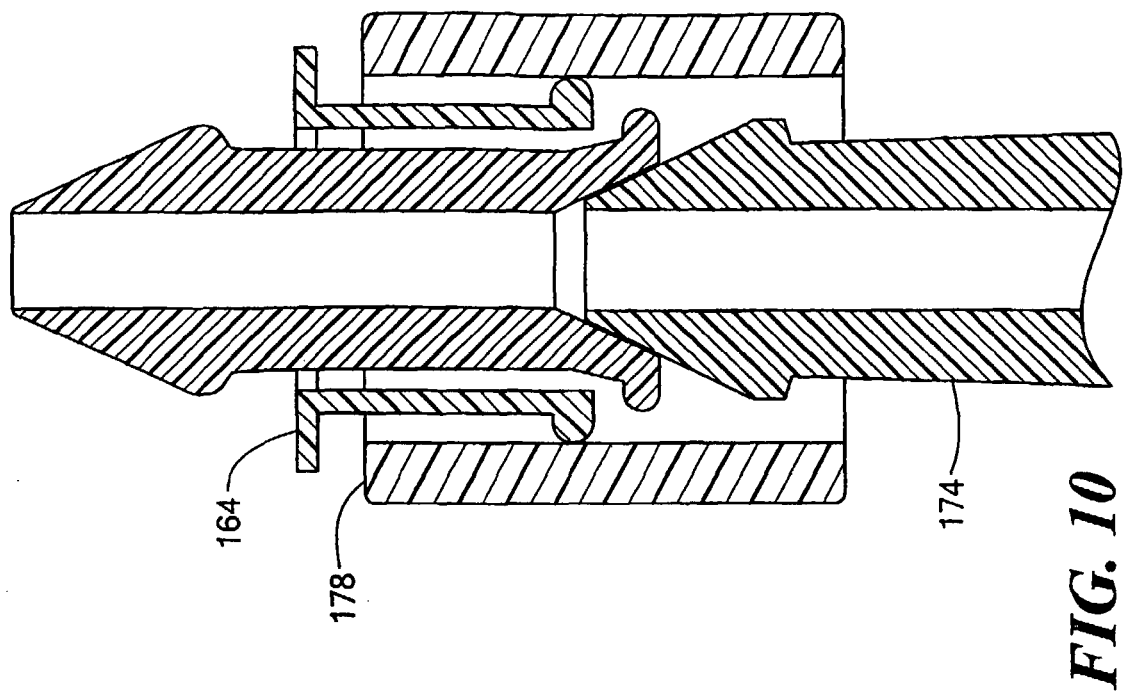
FIG. 10 is a cross sectional side view of a still further embodiment of a quick connector assembly of the present invention.
Figure 9:
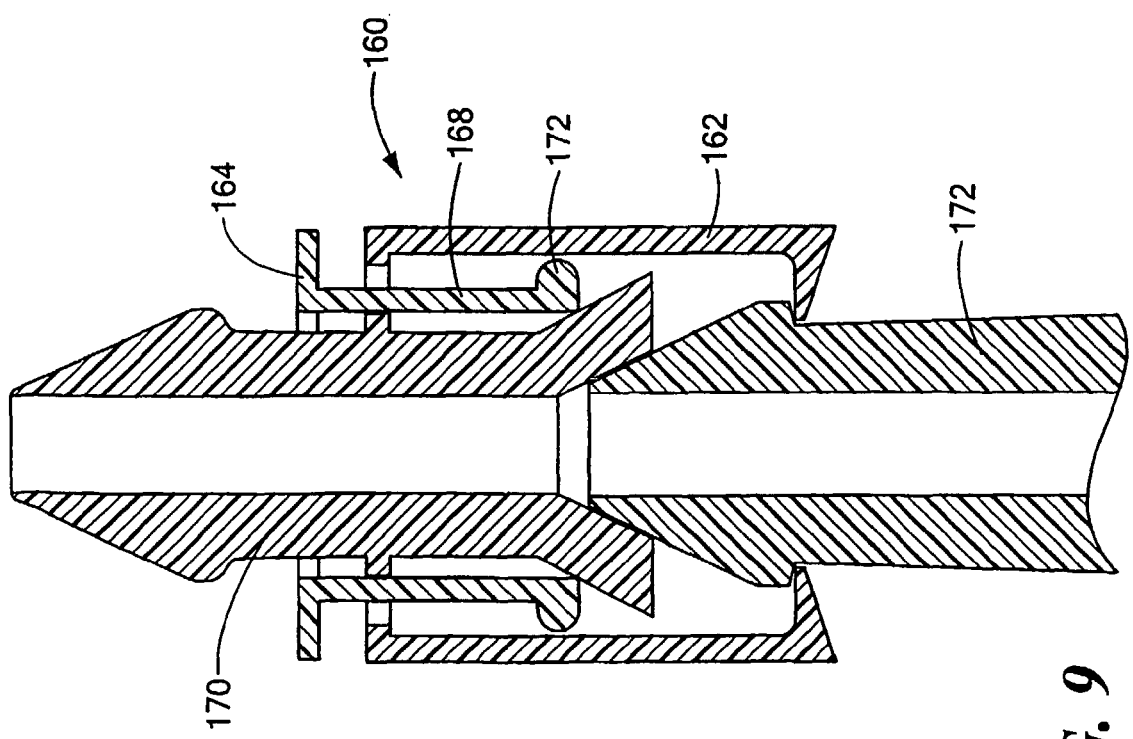
FIG. 9 is a cross sectional side view of a still further embodiment of a quick connector assembly of the present invention.

FIG. 9 illustrates a further embodiment of a quick connector assembly 160 having locking arms 162, such as described with respect to FIG. 8. A collar 164 having collar arms 168 is slipped over the end of a connector body 170. Ribs 172 on the ends of the collar arms 168 press on the body 170 to provide a seal against the barb element 174 of a shunt system. Disconnection is made by pressing the collar 164 downwardly, thereby dislodging the locking arms 162 from the barb element. To provide a smooth outer surface, a shell 178 can be added to the connector assembly of FIG. 9. See FIG. 10. The shell helps to reduce tissue growth to the connector assembly.

Figure 11:
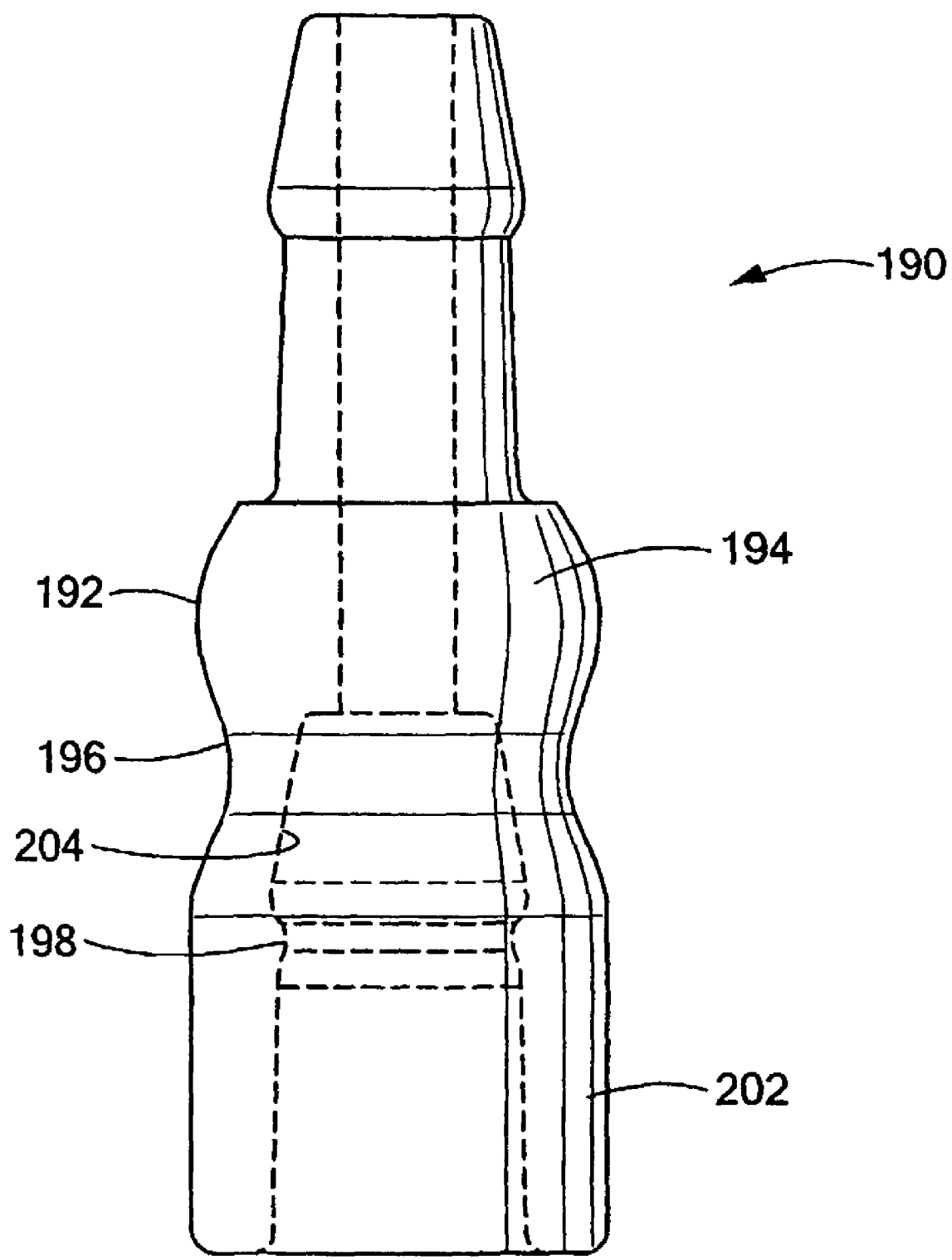
FIG. 11 is a cross sectional side view of a still further embodiment of a quick connector assembly of the present invention.

A further one-piece embodiment of a quick connector assembly 190 is illustrated in FIG. 11. The outer surface 192 of the connector body 194 includes a finger grip region 196. A locking ring or rib 198 is formed integrally with an internal surface within a female portion 202. The internal surface can include a tapered or conical section 204 to provide a seal with the barb element (not shown).

The quick connector assembly can be manufactured in any suitable manner such as by injection molding, and can be made of any suitable biocompatible material, such as silicone or a silicone-based material or polyethersulfone. The material must resist corrosion. Preferably, the materials are selected for compatibility with sterilization by ethylene-oxide (EtO) and steam processes. A metal material, such as stainless steel, can be used, although plastic and silicone-based materials are preferred if the materials should not be detected by MRI scanning. These materials are also fairly easy to manufacture, such as by injection molding. The shunt connection can be impregnated with antibiotics to prevent or minimize infection. The shunt connection can be impregnated with barium or can include a barium stripe to allow the shunt to be visible on X-rays.

The present quick connector assembly features a positive locking system to ensure that the surgeon makes a proper connection. The connection provides an audible sound, such as a click or snap, allowing the surgeon to hear that the connection has been made.

The shunt connector assembly provides a simpler procedure for implanting shunts by eliminating some of the time and struggle involved with suturing the catheter to the shunt. Shortening surgery time and limiting contact with the shunt also minimizes opportunities for infection. If a shunt needs to be replaced, reinstallation time is also minimized by the ability to leave the catheters in place and simply swap out the shunt. The quick connector assembly can be used on either the proximal or distal (inlet or outlet) side of the valve housing of a shunt system.

The invention is not to be limited by what has been particularly shown and described, except as indicated by the appended claims.

What is claimed is:

1. A quick connector assembly for connection to a hydrocephalus shunt system, the hydrocephalus shunt system including a valve in a valve housing, a barb element having an external barb, and a catheter, the quick connector assembly comprising:
   a connector body comprising a main body portion, a fluid passage extending through the main body portion in a linear direction from an entrance opening to an exit opening, the catheter affixable to the main body portion of the connector body at the exit opening;
   the main body portion comprising an interior defined by an interior wall separated by shoulders into a first section, a second section, and a third section;
   a resilient holding element comprising a radially inwardly projecting member disposed to resile after passage of the external barb to retain the external barb of the barb element with at least a portion of the barb element in a connected position within the connector body, the holding element further comprising an annular ring, having a split therein, disposed within the second section between the first and third sections of the main body portion of the connector body to substantially circumferentially surround the barb element adjacent the external barb when the barb element is in the connected position;
   a sealing element disposed within the third section of the main body portion to provide a fluid seal against the barb element in the connected position; and
   a retaining insert disposed within the first section of the main body portion of the connector body, the retaining insert including a surface transverse to the direction of the fluid passage and facing the annular ring, the annular ring retained within the main body portion by abutment against the facing transverse surface of the retaining insert.

2. The assembly of claim 1, wherein the retaining insert has an internal shape that conforms to a shape of a portion of the barb element inserted therein.

3. The assembly of claim 1, wherein the annular ring is retained in an annular groove in an interior surface in the second section of the connector body.

4. The assembly of claim 1, wherein the holding element is restrained from moving axially in the direction of the fluid passage in the connector body.

5. The assembly of claim 1, wherein the sealing element comprises an O-ring disposed within the connector body in contact with the barb element.

6. The assembly of claim 1, wherein the sealing element comprises a sealing surface formed by an internal surface of the connector body.

7. The assembly of claim 1, wherein the sealing element comprises a tapered internal surface of the connector body.

8. The assembly of claim 1, wherein the sealing element comprises a smooth internal surface of the connector body.

9. The assembly of claim 1, wherein the connector body includes a smooth exterior surface.

10. The assembly of claim 1, wherein one end of the connector body comprises a male portion to which the catheter is affixed.

11. The assembly of claim 1, wherein the catheter is adhesively affixed to one end of the connector body.

12. A quick connector assembly for connection to a hydrocephalus shunt system, the hydrocephalus shunt system including a valve in a valve housing, a barb element having an external barb, and a catheter, the quick connector assembly comprising:
    a connector body comprising a one-piece body, a fluid passage extending through the one-piece body, the catheter affixable to one end of the one-piece body;
    a resilient holding element comprising a radially inwardly projecting member disposed to resile after passage of the external barb to retain the external barb of the barb element with at least a portion of the barb element in a connected position within the one-piece body, wherein the holding element comprises an annular rib unitary with the one-piece body and integrally formed in an interior surface of the one-piece body; and
    a sealing element disposed to provide a fluid seal against the barb element in the connected position, wherein the sealing element comprises a sealing surface formed by a smooth, tapered section of the internal surface of the one-piece body.

13. The assembly of claim 12, wherein the connector body includes a smooth exterior surface.

14. A shunt system comprising:
    the quick connector assembly of claim 12;
    a hydrocephalus shunt system comprising:
        a valve housing having a valve therein,
        a barb element having an external barb extending from the valve housing, the barb element insertable in the connector body of the quick connector assembly with the barb element retainable by the holding element, and
        a catheter affixed to the end of the quick connector assembly.

15. A method for connecting a catheter to a hydrocephalus shunt system, comprising:
    providing the quick connector assembly of claim 12 with the catheter affixed to the end of the connector body; and
    inserting a barb element into the connector body until an external barb on the barb element is retained beneath the holding element of the quick connector assembly.

16. A quick connector assembly for connection to a hydrocephalus shunt system, the hydrocephalus shunt system including a valve in a valve housing, a barb element having an external barb, and a catheter, the quick connector assembly comprising:
    a connector body having a fluid passage extending therethrough, the catheter affixable to one end of the connector body;
    a resilient holding element comprising a radially inwardly projecting member disposed to resile after passage of the external barb to retain the external barb of the barb element with at least a portion of the barb element in a connected position within the connector body, wherein the holding element comprises a plurality of resilient arms attached to the connector body, the radially inwardly projecting member disposed at the end of each resilient arm, and wherein the resilient arms comprise lever arms attached to the connector body with a fulcrum extension at a midregion of the lever arms; and a sealing element disposed to provide a fluid seal against the barb element in the connected position.

17. The assembly of claim 16, wherein the radially inwardly projecting member comprises a tooth element.

18. The assembly of claim 16, wherein the sealing element comprises a sealing surface formed by an internal surface of the connector body.

19. The assembly of claim 16, wherein the connector body includes a smooth exterior surface.

20. A shunt system comprising:
the quick connector assembly of claim 16;
a hydrocephalus shunt system comprising:
a valve housing having a valve therein,
a barb element having an external barb extending from the valve housing, the barb element insertable in the connector body of the quick connector assembly with the barb element retainable by the holding element, and
a catheter affixed to the end of the quick connector assembly.

21. A method for connecting a catheter to a hydrocephalus shunt system, comprising:
providing the quick connector assembly of claim 16 with the catheter affixed to the end of the connector body; and
inserting a barb element into the connector body until an external barb on the barb element is retained beneath the holding element of the quick connector assembly.

22. A quick connector assembly for connection to a hydrocephalus shunt system, the hydrocephalus shunt system including a valve in a valve housing, a barb element having an external barb, and a catheter, the quick connector assembly comprising:
a connector body having a fluid passage extending therethrough, the catheter affixable to one end of the connector body;
a resilient holding element comprising a radially inwardly projecting member disposed to resile after passage of the external barb to retain the external barb of the barb element with at least a portion of the barb element in a connected position within the connector body, wherein the holding element comprises a plurality of resilient arms attached to the connector body, the radially inwardly projecting member disposed at the end of each resilient arm, and wherein the resilient arms are attached to the connector body at an opposite end of the arms and the resilient arms are pinchable radially inwardly to move the projecting members outwardly to release the external barb; and a sealing element disposed to provide a fluid seal against the barb element in the connected position.

23. The assembly of claim 22, wherein the sealing element comprises a sealing surface formed by an internal surface of the connector body.

24. The assembly of claim 22, wherein the connector body includes a smooth exterior surface.

25. A shunt system comprising:
the quick connector assembly of claim 22;
a hydrocephalus shunt system comprising:
a valve housing having a valve therein,
a barb element having an external barb extending from the valve housing, the barb element insertable in the connector body of the quick connector assembly with the barb element retainable by the holding element, and
a catheter affixed to the end of the quick connector assembly.

26. A method for connecting a catheter to a hydrocephalus shunt system, comprising:
providing the quick connector assembly of claim 22 with the catheter affixed to the end of the connector body; and
inserting a barb element into the connector body until an external barb on the barb element is retained beneath the holding element of the quick connector assembly.

27. The assembly of claim 22, wherein the radially inwardly projecting member comprises a tooth element.

28. A shunt system comprising:
the quick connector assembly of claim 1;
a hydrocephalus shunt system comprising:
a valve housing having a valve therein,
a barb element having an external barb extending from the valve housing, the barb element insertable in the connector body of the quick connector assembly with the barb element retainable by the holding element, and
a catheter affixed to an end of the quick connector assembly.

29. A method for connecting a catheter to a hydrocephalus shunt system, comprising:
providing the quick connector assembly of claim 1 with the catheter affixed to the main body portion of the connector body; and
inserting a barb element into the connector body until an external barb on the barb element is retained beneath the holding element of the quick connector assembly.

30. The method of claim 29, wherein the step of inserting the barb element into the connector body produces an audible sound when the barb element passes the holding element to provide an indication that the barb element is retained beneath the holding element.

* * * * *